United States Patent [19]

Stetter et al.

[11] 4,359,469
[45] Nov. 16, 1982

[54] COMBATING PESTS WITH N-SULPHENYLATED OXIME-CARBAMATES

[75] Inventors: Jörg Stetter, Wuppertal; Bernhard Homeyer, Leverkusen; Ingeborg Hammann, Cologne, all of Fed. Rep. of Germany

[73] Assignee: Bayer Aktiengesellschaft, Leverkusen, Fed. Rep. of Germany

[21] Appl. No.: 819,021

[22] Filed: Jul. 25, 1977

[30] Foreign Application Priority Data

Aug. 10, 1976 [DE] Fed. Rep. of Germany ....... 2635883

[51] Int. Cl.³ .................. A01N 47/24; C07D 233/61; C07D 231/12; C07D 249/08
[52] U.S. Cl. ............................... 424/269; 424/273 R; 424/273 B; 424/273 P; 424/273 N; 548/255; 548/259; 548/260; 548/262; 548/263; 548/265; 548/267; 548/268; 548/329; 548/332; 548/333; 548/337; 548/338; 548/339; 548/341; 548/372; 548/377; 548/378
[58] Field of Search .................... 260/308 R; 548/341, 548/255, 259, 260, 263, 264, 265, 267, 268, 329, 332, 333, 337, 338, 339, 341, 372, 371, 377, 378; 424/269, 273 R, 273 P, 273 B, 273 N

[56] References Cited

U.S. PATENT DOCUMENTS

| | | | |
|---|---|---|---|
| 3,394,143 | 7/1968 | Wolf | 260/308 R |
| 3,812,142 | 5/1974 | Meiser et al. | 260/309 |
| 3,823,159 | 7/1974 | Karten | 424/273 |
| 3,897,438 | 7/1975 | Draber et al. | 260/308 R |
| 4,014,915 | 3/1977 | Itoh | 260/308 R |

Primary Examiner—Alton D. Rollins

Attorney, Agent, or Firm—Sprung, Horn, Kramer & Woods

[57] ABSTRACT

N-Sulphenylated oxime-carbamates of the formula

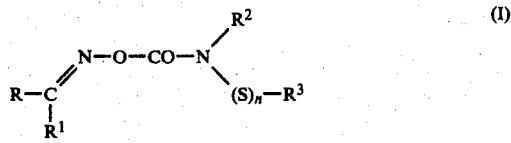

in which
R is alkyl or optionally substituted cycloalkyl, aryl or aralkyl,
$R^1$ is an optionally substituted N-containing heterocyclic radical or an alkyl or cycloalkyl radical substituted by an optionally substituted N-containing heterocyclic radical,
$R^2$ is alkyl,
$R^3$ is alkyl, halogenoalkyl, optionally substituted phenyl or alkoxycarbonyl, a radical identical to that to which the —(S)$_n$—$R^3$ group is bonded, or

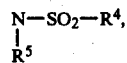

$R^4$ is alkyl, dialkylamino or optionally substituted phenyl,
$R^5$ is alkyl, and
n is 1 or 2, and their salts, which possess arthropodicidal, nematicidal and fungicidal properties.

9 Claims, No Drawings

COMBATING PESTS WITH N-SULPHENYLATED OXIME-CARBAMATES

The present invention relates to and has for its objects the provision of particular new N-sulphenylated oxime-carbamates which possess arthropodicidal, nematicidal and fungicidal properties, active compositions in the form of mixtures of such compounds with solid and liquid dispersible carrier vehicles, and methods for producing such compounds and for using such compounds in a new way especially for combating pests, e.g. arthropods, nematodes and fungi, with other and further objects becoming apparent from a study of the within specification and accompanying examples.

It has been disclosed in German DOS No. 1,567,142 that certain α-cyano-oxime-carbamates, such as, for example, 1-cyano-2-methyl-propan-aldoxime-N-methylcarbamate (Compound A) and 1-cyano-butanal-aldoxime-N-methylcarbamate (Compound B), possess pesticidal, especially insecticidal and nematicidal, properties. Their action, however, is not always entirely satisfactory, especially when low amounts are used.

Furthermore, it has in been disclosed in German DOS No. 2,111,156 that certain 3-hydroxy-2,2-dimethylpropanal-oxime-carbamates, such as, for example, 3-hydroxy-2,2-dimethylpropanal-(O-methylcarbamoyl-oxime) (Compound C), are insecticidally active. However, their action is also not always entirely satisfactory, especially if low amounts are used.

The present invention now provides, as new compounds, the N-sulphenylated oxime-carbamates of the general formula

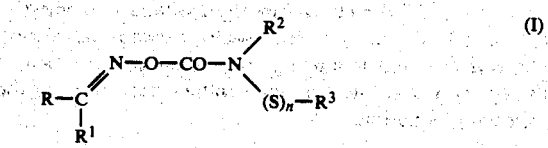

in which
R is alkyl or optionally substituted cycloalkyl, aryl or aralkyl,
$R^1$ is an optionally substituted N-containing heterocyclic radical or an alkyl or cycloalkyl radical substituted by an optionally substituted N-containing heterocyclic radical,
$R^2$ is alkyl,
$R^3$ is alkyl, halogenoalkyl, optionally substituted phenyl or alkoxycarbonyl, a radical identical to that to which the $—(S)_n—R^3$ group is bonded, or

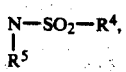

$R^4$ is alkyl, dialkylamino or optionally substituted phenyl,
$R^5$ is alkyl, and
n is 1 or 2,
and their salts.

Preferably, R represents straight-chain or branched alkyl with 1 to 6 carbon atoms, phenyl, which can optionally be substituted by halogen (especially fluorine, chlorine or bromine), phenylalkyl which has 1 to 4 carbon atoms in the alkyl part and which is optionally substituted in the phenyl part by halogen (especially fluorine, chlorine or bromine), or optionally methyl- or ethyl-substituted cycloalkyl with 5 to 7 carbon atoms;

$R^1$ represents a pyrazol-1-yl, imidazol-1-yl, 1,2,4-triazol-1-yl, 1,2,3-triazol-1-yl, 1,3,4-triazol-1-yl, 1,2,5-triazol-1-yl, indazol-1-yl, benzimidazol-1-yl, or benztriazol-1-yl radical which optionally carries one or more substituents selected from halogen (especially fluorine, chlorine and bromine), alkyl with 1 to 4 carbon atoms, halogenoalkyl with up to 2 carbon atoms and up to 5 halogen atoms (especially fluorine and chlorine atoms, tri-fluoromethyl being an example), alkoxy and alkylthio each with up to 4 carbon atoms, and the nitro group, or $R^1$ represents alkyl with 1-4 carbon atoms or cycloalkyl with 5-6 carbon atoms, either of which is substituted by a pyrazol-1-yl, imidazol-1-yl, 1,2,4-triazol-1-yl, 1,2,3-triazol-1-yl, 1,3,4-triazol-1-yl, 1,2,5-triazol-1-yl, indazol-1-yl, benzimidazol-1-yl, or benztriazol-1-yl radical which optionally carries one or more substituents selected from halogen (especially fluorine, chlorine and bromine), alkyl with 1 to 4 carbon atoms, halogenoalkyl with up to 2 carbon atoms and up to 5 halogen atoms (especially fluorine and chlorine atoms, tri-fluoromethyl being an example), alkoxy and alkylthio each with up to 4 carbon atoms and the nitro group;

$R^2$ represents straight-chain or branched alkyl with 1 to 4 carbon atoms;

and $R^3$ represents alkyl with 1 to 4 carbon atoms, halogenoalkyl with 1 or 2 carbon atoms and up to 5 halogen atoms (especially fluorine and chlorine atoms, examples being tri-fluoromethyl, chlorodifluoromethyl, dichlorofluoromethyl and trichloromethyl), phenyl which is optionally substituted by halogen (especially fluorine, chlorine or bromine), alkyl with 1 or 2 carbon atoms or halogenoalkyl with 1 or 2 carbon atoms and up to 5 halogen atoms (especially fluorine and chlorine atoms, an example being the trifluoromethyl group), or represents alkoxycarbonyl with 1 to 4 carbon atoms in the alkoxy part or a radical identical to that to which the $—(S)_nR^3$ group is bonded, or represents the $—NR^5—SO_2—R^4$ radical, in which $R^5$ represents alkyl with 1 to 4 carbon atoms and $R^4$ represents alkyl with 1 to 4 carbon atoms, dialkylamino with 1 to 4 carbon atoms in each alkyl part, or phenyl which is optionally substituted by halogen (especially fluorine, chlorine or bromine), alkyl with 1 or 2 carbon atoms, halogenoalkyl with 1 or 2 carbon atoms and up to 5 halogen atoms (especially fluorine and chlorine atoms, trifluoromethyl being an example), cyano or nitro.

The compounds of the formula (I) can be present in the syn-form or the anti-form; predominantly, they arise as mixtures of both forms.

Preferred salts of the compounds of the formula (I) are, from the point of view of phytotoxicity salts with physiologically tolerated acids. These preferably include the hydrogen halide acids such as, for example, hydrobromic acid and especially hydrochloric acid), phosphoric acid, nitric acid, monofunctional and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and 1,5-naphthalene-disulphonic acid.

Surprisingly, the N-sulphenylated oxime-carbamates according to the invention exhibit a higher insecticidal, acaricidal and nematocidal action than the known carbamates 1-cyano-2-methylpropanaldoxime-N-methylcarbamate and 1-cyano-butanaldoxime-N-methylcarbamate as well as 3-hydroxy-2,2-dimethylpropanal-(O-methylcarbamoyloxime), which chemically, and in terms of their action, are close compounds. The active compounds according to the invention thus represent an enrichment of the art.

The invention also provides a process for the preparation of an N-sulphenylated oxime-carbamate of the formula (I), in which (a) an oxime of the general formula

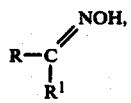    (II)

in which R and R¹ have the above-mentioned meanings, is reacted with a sulphenylated carbamoyl halide of the general formula

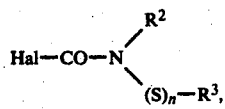    (III)

in which R², R³ and n have the above-mentioned meanings and Hal represents fluorine or chlorine, in the presence of a diluent and of an acid-binding agent, or (b) an oxime-carbamate of the general formula

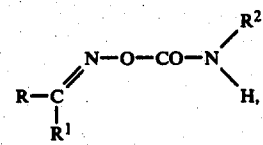    (IV)

in which R, R¹ and R² have the above-mentioned meanings, is reacted with a sulphene chloride of the general formula

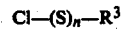    (V), in which R³ and n have the above-mentioned meanings, in the presence of a diluent and of an acid-binding agent.

If 3,3-dimethyl-2-oximino-1-(1,2,4-triazol-1-yl)butane and N-methyl-N-trichloromethylmercapto-carbamoyl fluoride are used starting materials in process variant (a), the course of the reaction can be represented by the following equation:

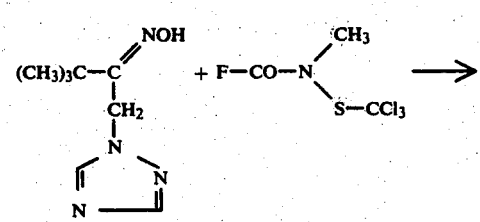

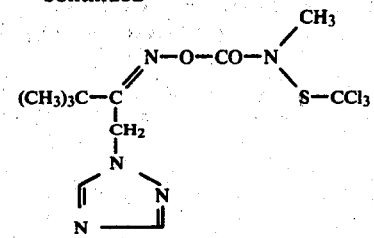

If 2,2-dimethyl-1-(imidazol-1-yl)-1-oximino-propane and N,N'-bis-(fluorocarbonyl)-thio-bis-methylamine are used as starting materials in process variant (a), the course of the reaction can be represented by the following equation:

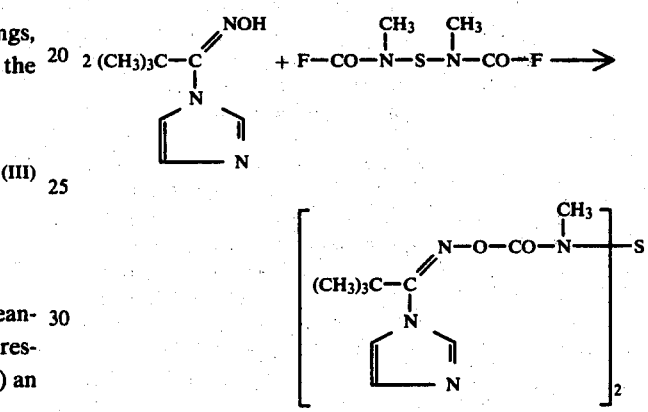

If 2,2-dimethyl-1-methylcarbamoyloximino-1-(pyrazol-1-yl)-propane and 4-chlorophenyl-sulphenyl chloride are used as starting materials in process variant (b), the course of the reaction can be represented by the following equation:

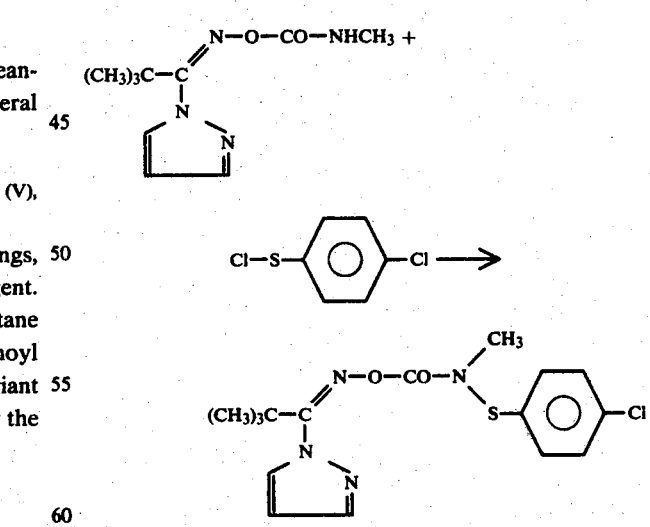

The following may be mentioned as examples of starting materials of the formula (II): 3,3-dimethyl-2-oximino-1-pyrazol-1-yl-butane, 3,3-dimethyl-1-imidazol-1-yl-2-oximino-butane, 3,3-dimethyl-2-oximino-1-(1,2,4-triazol-1-yl)-butane, 3,3-dimethyl-2-oximino-1-(1,2,3-triazol-1-yl)-butane, 3,3-dimethyl-2-oximino-1-(1,3,4-triazol-1-yl)-butane, 3,3-dimethyl-1- indazol-1-yl-2-oximinobutane, 1-benzimidazol-1-yl-3,3-di-methyl-2-oximino-butane, 1-benztriazol-1-yl-3,3-dimethyl-2-oximino-butane, 2-oximino-1-pyrazol-1-yl-propane, 2-oximino-1-(1,2,4-triazol-1-yl)propane, 1-imidazol-1-yl-2-oximino-propane, 3-methyl-2-oximino-1-pyrazol-1-yl-butane, 1-imidazolyl-3-methyl-2-oximino-ethane, 3-methyl-2-oximino-1-(1,2,4-triazol-1-yl)-butane, 2-oximino-2-phenyl-1-pyrazol-1-yl-ethane, 1-imidazol-1-yl-2-oximino-2-phenyl-ethane, 2-oximino-2-phenyl-1-(1,2,4-triazol-1-yl)-ethane, 2-oximino-2-phenyl-1-(1,2,3-triazol-1-yl)-ethane, 2-oximino-2-phenyl-1-(1,3,4-triazol-1-yl)-ethane, 2-(4-chlorophenyl)-1-imidazol-1-yl-2-oximinoethane, 2-(2,4-dichlorophenyl)-2-oximino-1-(1,2,4-triazol-1-yl)-ethane, 2-oximino-3-phenyl-1-pyrazol-1-yl-propane, 3-(4-bromophenyl)-1-imidazol-1-yl-2-oximino-propane, 3,3-dimethyl-2-oximino-3-phenyl-1-(1,2,4-triazol-1-yl)propane, 2-cyclopentyl-1-imidazol-1-yl-2-oximino-ethane, 2-cyclohexyl-1-imidazol-1-yl-2-oximino-ethane, 2-cyclohexyl-2-oximino-1-pyrazol-1-yl-ethane, 2-cyclohexyl-2-oximino-1-(1,2,4-triazol-1-yl)-ethane, 1-benzimidazol-1-yl-2-cyclohexyl-2-oximino-ethane, 2-cycloheptyl-2-oximino-1-pyrazol-1-yl-ethane, 1-imidazol-1-yl-2-(methylcyclohexyl)-2-oximino-ethane, 1-(4-chloropyrazol-1-yl)-3,3-dimethyl-2-oximino-butane, 1-(3-acetyl-pyrazol-1-yl)-3,3-dimethyl-2-oximino-butane, 1-(2-bromoimidazol-1-yl)-3,3-dimethyl-2-oximino-butane, 3,3-dimethyl-1-(2-methyl-imidazol-1-yl)-2-oximino-butane, 3,3-dimethyl-2-oximino-(4-trifluoromethylimidazol-1-yl)-butane, 3,3-dimethyl-1-(4-nitroimidazol-1-yl)-2-oximino-butane, 1-(3-chloro-1,2,4-triazol-1-yl)-3,3-dimethyl-2-oximino-butane, 1-(3-ethyl-1,2,4-triazol-1-yl)-3,3-dimethyl-2-oximino-butane, 3,3-dimethyl-1-methyl-2-oximino-1-pyrazol-1-yl-butane, 3,3-dimethyl-1-imidazol-1-yl-1-methyl-2-oximino-butane, 3,3-dimethyl-1-methyl-2-oximino-1-(1,2,4-triazol-1-yl)-butane, 1,1-dimethyl-2-oximino-1-(1,2,4-triazol-1-yl)-propane, 1,1-dimethyl-2-oximino-1-pyrazol-1-yl-propane, 1,1-dimethyl-3-methyl-2-oximino-1-(1,2,4-triazol-1-yl)-butane, 3,3-dimethyl-1-(5-methyl-4-nitro-imidazol-1-yl)-2-oximinobutane, 3,3-dimethyl-2-oximino-1-(3-trichloromethyl-1,2,4-triazol-1-yl)-butane, 1-(3-bromo-1,2,4-triazol-1-yl)-3,3-dimethyl-2-oximino-butane, 3,3-dimethyl-2-oximino-1-(2,4,5-tribromo-imidazol-1-yl)-butane, 2,2-dimethyl-1-oximino-pyrazol-1-yl)-butane, 2,2-dimethyl-1-oximinopyrazol-1-yl-propane, 2,2-dimethyl-1-imidazol-1-yl-oximino-propane, 2,2-dimethyl-1-oximino-1-(1,2,4-triazol-1-yl)-propane, 2,2-dimethyl-1-oximino-1-(1,2,3-triazol-1-yl)-propane, 2,2-dimethyl-1-oximino-2-(1,3,4-triazol-1-yl)-propane, 2-dimethyl-1-indazol-1-yl-1-oximino-propane, 1-benzimidazol-1-yl-2,2-dimethyl-1-oximino-propane, 1-benztriazol-1-yl-2,2-dimethyl-1-oximino-propane, 1-oximino-1-pyrazol-1-yl-ethane, 1-oximino-1-(1,2,4-triazol-1-yl)-ethane, 1-imidazol-1-yl-1-oximino-ethane, 2-methyl-1-oximino-1-pyrazol-1-yl-propane, 1-imidazol-yl-2-methyl-1-oximino-propane, 2-methyl-1-oximino-1-(1,2,4-triazol-1-yl)-propane, oximino-phenyl-pyrazol-1-yl-methane, imidazol-1-yl-oximino-phenyl-methane, oximino-phenyl-(1,2,4-triazol-1-yl)-methane, oximino-phenyl-(1,2,3-triazol-1-yl)-methane, oximino-phenyl-(1,3,4-triazol-1-yl)-methane, (4-chlorophenyl)imidazol-1-yl-oximino-methane, (2,4-dichlorophenyl)-oximino-(1,2,4-triazol-1-yl)-methane, 1-oximino-2-phenyl-1-pyrazol-1-yl-ethane, (4-bromophenyl)-1-imidazol-1-yl-1-oximino-ethane, 2,2-dimethyl-1-oximino-2-phenyl-1-(1,2,4-triazol-1-yl)-ethane, cyclopentyl-imidazol-1-yl-oximino-methane, cyclohexyl-imidazol-1-yl-oximino-methane, cyclohexyloximino-pyrazol-1-yl-methane, cyclohexyl-oximino-(1,2,4-triazol-1-yl)-methane, benzimidazol-1-yl-cyclohexyl-oximino-methane, cycloheptyl-oximino-pyrazol-1-yl-methane, imidazol-1-yl-(methylcyclohexyl)-oximino-methane, 1-(4-chloropyrazol-1-yl)-2,2-dimethyl-1-oximino-propane, 1-(3-acetylpyrazol-1-yl)-2,2-dimethyl-1-oximino-propane, 1-(2-bromoimidazol-1-yl)-2,2-dimethyl-1-oximino-propane, 2,2-dimethyl-1-(2-methylimidazol-1-yl)-1-oximino-propane, 2,2-dimethyl-1-oximino-(4-trifluoromethylimidazol-1-yl)-propane, 2,2-dimethyl-1-(4-nitroimidazol-1-yl)-1-oximinopropane, 1-(3-chloro-1,2,4-triazol-1-yl)-2,2-dimethyl-1-oximino-propane, 1-(3-ethyl-1,2,4-triazol-1-yl)-2,2-dimethyl-1-oximino-propane, 2,2-dimethyl-1-methyl-1-oximino-1-pyrazol-1-yl-propane, 2,2-dimethyl-1-(5-methyl-4-nitroimidazol-1-yl)-1-oximino-propane, 2,2-dimethyl-1-oximino-1-(3-trichloromethyl-1,2,4-triazol-1-yl)-propane, 1-(3-bromo-1,2,4-triazol-1-yl)-2,2-dimethyl-1-oximinopropane and 2,2-dimethyl-1-oximino-1-(2,4,5-tribromoimidazol-1-yl)-propane.

The oximes of the formula (II) are described in U.S. patent application Ser. No. 782,263 filed Mar. 25, 1977, now abandoned.

The oximes of the formula (II), in which $R^1$ represents an optionally substituted N-containing heterocyclic radical, can be prepared by reacting hydroxamic acid halides of the general formula

in which

R has the above-mentioned meaning and

Hal represents halogen, especially chlorine or bromine, with azoles of the formula

in which $R^1$ represents an optionally substituted heterocyclic radical, in the presence of an organic solvent, for example tetrahydrofuran, and in the presence of an acid-binding agent, for example trimethylamine or excess azole, at temperatures between 0° and 80° C., preferably 0° and 40° C. The compounds of the formula (II) are isolated by adding water to the reaction mixture, filtering off and drying the resulting precipitate, and purifying it, if appropriate, by recrystallization.

The hydroxamic acid halides of the formula (VI) used as starting materials are in general known (see H. Ulrich "The Chemistry of Imidoyl Halides", pages 157–172, Plenum Press, New York, 1968 and the literature references cited therein). Those not yet known can easily be prepared in accordance with the processes described there, such as, for example, by chlorinating the corresponding aldoximes.

The oximes of the formula (II), in which $R^1$ represents an alkyl or cycloalkyl radical which is substituted by an optionally substituted N-containing heterocyclic radical, can be prepared, for example, by reacting azolyl-ketones of the general formula

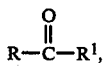

in which R and R¹ have the above mentioned meanings, with hydroxylamine in the presence of a solvent, preferably an alcohol or aqueous alcohol, at temperatures between 20° and 100° C., preferably between 50° and 80° C. In this reaction, the hydroxylamine is preferably employed in the form of its salts, especially as the hydrochloride, in the presence of an acid-binding agent such as, for example, sodium carbonate. The compounds of the formula (II) are isolated by working up the product, formed during the reaction, in accordance with customary methods after distilling off the solvent.

Azolyl-ketones of the formula (VIII) used as starting materials in this reaction are disclosed in German Published Specification DOS No. 2,431,407. They can be prepared by reacting halogenoketones of the general formula

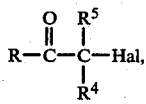

in which

R has the above-mentioned meaning and

R⁴ and R⁵ each independently is hydrogen or alkyl, or conjointly are pentamethylene or tetramethylene, and Hal represents chlorine or bromine, with azoles of the formula (VII) in the presence of a diluent, for example, methyl ethyl ketone, and in the presence of an acid-binding agent, for example potassium carbonate, at temperatures between 20° and 150° C., preferably between 60° and 120° C. The compounds of the formula (IX) are isolated by filtering off the salt formed during the reaction and concentrating the filtrate by distilling off the solvent. The solid which thereupon remains is dried and purified by recrystallization.

Halogenoketones of the formula (IX) to be used as starting materials are known and can be prepared as described in de la Societe de la Chimique de France 1955, pages 1363–1383; Houben-Weyl "Methoden der Organischen Chemie" ("Methods of Organic Chemistry"), volume VII/2a, page 117; Beilstein "Handbuch der Organischen Chemie" ("Handbook of Organic Chemistry"), H 1, page 703, E I, pages 350, 261 and 364, EII, pages 738, 756 and 757 and E III pages 2842 and 2843.

The following may be mentioned as examples of starting materials of the formula (III): N-fluorodichloromethylsulphenyl-N-phenyl-carbamic acid fluoride, N,N'-bis-(fluorocarbonyl)-thio-bis-methylamine, N-methyl-N-trichloromethylsulphenyl-carbamic acid fluoride, N-methyl-N-fluorodichloromethylsulphenyl-carbamic acid fluoride, N-methyl-N-chlorodifluoromethylsulphenyl-carbamic acid fluoride, N-methyl-N-(3-trifluoromethylphenyl)-sulphenyl-carbamic acid fluoride, N-methyl-N-(methoxycarbonyl-sulphenyl)-carbamic acid fluoride, N-methyl-N-[(3-methylphenylsulphonyl)-methylamino-sulphenyl]-carbamic acid fluoride, N-methyl-N-(4-chlorophenyl)-sulphenyl-carbamic acid fluoride, N-methyl-N-[(4-methylphenyl-sulphonyl)-methylamino-sulphenyl]-carbamic acid fluoride and the corresponding carbamic acid chlorides.

Sulphenylated carbamoyl halides of the formula (III) are known or can be prepared in accordance with generally customary and known processes. They are obtained, for example, by reacting the corresponding carbamic acid halides with the corresponding sulphene chlorides (see German Published Specification DAS No. 1,297,095, U.S. Pat. No. 3,939,192 and German Published Specification DOS No. 2,357,930, U.S. Pat. No. 3,968,232 and U.S. Pat. No. 4,008,328).

The following may be mentioned as examples of starting materials of the formula (IV): 3,3-dimethyl-2-methylcarbamoyl-oximino-1-(1,2,4-triazol-1-yl)-butane, 3,3-dimethyl-2-isopropyl-carbamoyloximino-1-(pyrazol-1-yl)-butane, 3,3-dimethyl-2-methyl-carbamoyloximino-1-(pyrazol-1-yl)-butane, 3,3-dimethyl-2-methyl-carbamoyloximino-1-(3-methyl-pyrazol-1-yl)-butane, 3,3-dimethyl-2-methylcarbamoyloximino-1-(4-bromo-pyrazol-1-yl)-butane, 3,3-dimethyl-2-methylcarbamoyloximino-1-(4-chloro-pyrazol-1-yl)-butane, 3,3-dimethyl-2-methylcarbamoyloximino-1-(imidazol-1-yl)-butane, 3,3-dimethyl-2-methylcarbamoyloximino-1-(2-ethyl-imidazol-1-yl)-butane, 3,3-dimethyl-2-methylcarbamoyloximino-1-(2-ethyl-4-nitro-imidazol-1-yl)-butane, 3,3-dimethyl-2-methyl-carbamoyloximino-1-(benzimidazol-1-yl)-butane, 3,3-dimethyl-2-methylcarbamoyloximino-1-(benz-1,2,3-triazol-1-yl)-butane, 3,3-dimethyl-2-methylcarbamoyloximino-1-(1,2,3-triazol-1-yl)-butane, 3,3-dimethyl-2-methylcarbamoyloximino-1-(3-methyl-1,2,4-triazol-1-yl)-butane, 3,3-dimethyl-2-methylcarbamoyloximino-1-(3-chloro-1,2,4-triazol-1-yl)-butane, 3,3-dimethyl-2-methyl-carbamoyloximino-1-(3-methylmercapto-1,2,4-triazol-1-yl)-butane, 3-methyl-2-methylcarbamoyloximino-1-(pyrazol-1-yl)-butane, 4-methyl-2-methylcarbamoyloximino-1-(pyrazol-1-yl)-pentane, 2-phenyl-2-methylcarbamoyloximino-1-(1,2,4-triazol-1-yl)-ethane, 3-methyl-3-phenyl-2-methylcarbamoyloximino-1-(1,2,4-triazol-1-yl)-butane, 3-methyl-2-methylcarbamoyloximino-1-(1,2,4-triazol-1-yl)-butane, 3,3-dimethyl-2-methylcarbamoyloximino-1-(4-nitro-5-methyl-imidazol-1-yl)-butane, 2,2-dimethyl-1-methylcarbamoyloximino-1-(1,2,3-triazol-1-yl)-propane, 2,2-dimethyl-1-methyl-carbamoyloximino-1-(pyrazol-1-yl)-propane, 2,2-dimethyl-1-methyl-carbamoyloximino-1-(3-methyl-pyrazol-1-yl)-propane, 2,2-dimethyl-1-methylcarbamoyloximino-1-(4-chloro-pyrazol-1-yl)-propane, 2,2-dimethyl-1-methylcarbamoyloximino-1-(1,2,4-triazol-1-yl)-propane, 2,2-dimethyl-1-methylcarbamoyloximino-1-(3-chloro-1,2,4-triazol-1-yl)-propane, 2,2-dimethyl-1-methylcarbamoyloximino-1-(3-methyl-1,2,4-triazol-1-yl)-propane, 2,2-dimethyl-1-methyl-carbamoyloximino-1-(3-ethoxycarbonyl-1,2,4-triazol-1-yl)-propane, 2,2-dimethyl-1-methylcarbamoyloximino-1-(3-methylmercapto-1,2,4-triazol-1-yl)-propane, 2-methyl-1-methylcarbamoyloximino-1-(pyrazol-1-yl)-propane and 2-methyl-1-methylcarbamoyloximino-1-(1,2,4-triazol-1-yl)-propane.

The oxime-carbamates of the formula are described in the above-mentioned U.S. application Ser. No. 782,263.

They can be prepared by reacting oximes of the formula (II) with known isocyanates in the generally customary manner in the presence of a diluent, for example methylene chloride, at temperatures between 0° and 100° C.

The following may be mentioned as examples of starting materials of the formula (V): trichloromethylsulphene chloride, dichlorofluoromethylsulphene chloride, chlorodifluoromethylsulphene chloride, trifluoromethylsulphene chloride, phenylsulphene chloride, 2,4-dichlorophenylsulphene chloride, 3-trifluoromethylphenylsulphene chloride, 3-methylphenylsulphene chloride, methylsulphenyl chloride, 4-chloro-3-trifluoromethyl-phenylsulphenyl chloride, methoxycarbonylsulphenyl chloride and ethoxycarbonylsulphenyl chloride.

The sulphenyl chlorides of the formula (V) are generally known compounds in organic chemistry.

The acid-addition salts of the compounds of the formula (I) can be obtained in a simple manner in accordance with customary methods of forming salts, for example by dissolving the base in ethers, for example diethyl ether, and adding the acid, for example phosphoric acid, and can be isolated in a known manner, for example by filtering off, and be purified if appropriate.

Preferred diluents for the reactions according to process variants (a) and (b) are all inert organic solvents, especially ketones, such as diethyl ketone, and especially acetone and methyl ethyl ketone: nitriles such as propionitrile and especially acetonitrile; alcohols, such as ethanol or isopropanol; ethers, such as tetrahydrofuran or dioxane; formamides, such as, in particular, dimethylformamide; and halogenated hydrocarbons, such as methylene chloride, carbon tetrachloride or chloroform.

The reactions according to process variants (a) and (b) are carried out in the presence of an acid-binding agent. All customarily usable inorganic and organic acid-binding compounds may be added, especially alkali metal carbonates, such as, for example, sodium carbonate, potassium carbonate and sodium bicarbonate, and also lower tertiary alkyl-amines, cycloalkylamines, such as, for example, triethylamine, N,N-dimethylbenzylamine and dicyclohexylamine, as well as pyridine and diazabicyclooctane.

In carrying out process variant (a), the reaction temperatures can be varied within a fairly wide range. In general, the reaction is carried out at from 0° to 100° C., preferably from 10° to 80° C.

In carrying out process variant (a), preferably 1 to 2 moles or, in the case of a dimeric product, 0.5 mole of carbamoyl chloride of the formula (III) and 1 to 2 moles of acid-binding agent are employed per mole of the compound of the formula (II). The compounds of the formula (I) are isolated in the generally customary and known manner.

The reaction temperatures for carrying out process variant (b) can be varied within a fairly wide range. In general, the reaction is carried out at from 0° to 100° C., preferably from 10° to 50° C.

In carrying out process variant (b), the starting materials are preferably employed in equimolar amounts. The compounds of the formula (I) are isolated in accordance with customary methods.

Active compounds according to the invention, of the formula (I), in which
R represents t-butyl,
R¹ represents imidazolyl or triazolyl optionally substituted by halogen or $C_1$-$C_4$ alkyl, or represents methyl which is substituted by optionally halogen-substituted or $C_1$-$C_4$ alkyl-substituted imidazolyl or triazolyl,
R² represents methyl, and
R³ represents halogenoalkyl, methoxycarbonyl, optionally halogen-, halogenoalkyl- or alkyl-substituted phenyl, a radical identical to that bonded to the group $(S)_n$—$R^3$, or the group

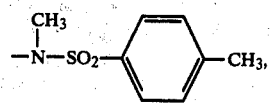

are particularly preferred.

The following may be mentioned as examples of particularly active representatives of the active compounds according to the invention: 2,2-dimethyl-1-(N-methyl-N-methylmercapto)-carbamoyloximino-1-(1,2,4-triazol-1-yl)-propane, 2,2-dimethyl-1-(N-methyl-N-methylmercapto)-carbamoyloximino-1-(pyrazol-1-yl)-propane, 2,2-dimethyl-1-(N-methyl-N-phenylmercapto)-carbamoyloximino-1-(1,2,4-triazol-1-yl)-propane, 2,2-dimethyl-1-(N-methyl-N-phenylmercapto)-carbamoyloximino-1-(pyrazol-1-yl)-propane, 2,2-dimethyl-1-[N-methyl-N-(4-chloro-3-trifluoromethyl-phenylmercapto)]-carbamoyloximino-1-(1,2,4-triazol-1-yl)-propane, 2,2-dimethyl-1-[N-methyl-N-(4-chloro-3-trifluoromethyl-phenylmercapto)]-carbamoyloximino-1-(pyrazol-1-yl)-propane, 2,2-dimethyl-1-(N-methyl-N-ethoxycarbonylmercapto)carbamoyloximino-1-(1,2,4-triazol-1-yl)-propane, 2,2-dimethyl-1-(N-methyl-N-ethoxycarbonylmercapto)-carbamoyloximino-1-(pyrazol-1-yl)-propane, 2,2-dimethyl-1-(N-methyl-N-ethoxycarbonylmercapto)-carbamoyloximino-1-(pyrazol-1-yl)-propane, 2,2-dimethyl-1-(N-methyl-N-fluorodichloromethylmercapto)-carbamoyloximino-1-(3-fluoro-1,2,4-triazol-1-yl)-propane, N,N'-bis-[2,2-dimethyl-1-oximinocarbonyl-1-(3-fluoro-1,2,4-triazol-1-yl)-propane]-thio-bis-methylamine, 2,2-dimethyl-1-[N-methyl-N-(3-trifluoromethylphenylmercapto)]-carbamoyloximino-1-(3-fluoro-1,2,4-triazol-1-yl)-propane, 2,2-dimethyl-1-[N-methyl-N-(3-trifluoromethylphenylmercapto)]-carbamoyloximino-1-(3-methyl-1,2,4-triazol-1-yl)-propane, 2,2-dimethyl-1-[N-methyl-N-(3-trifluoromethylphenylmercapto)]-carbamoyloximino-1-(3-methylmercapto-1,2,4-triazol-1-yl)-propane, 2-methyl-1-(N-methyl-N-methylmercapto)-carbamoyloximino-1-(1,2,4-triazol-1-yl)-propane, 2-methyl-1-(N-methyl-N-methylmercapto)-carbamoyloximino-1-(pyrazol-1-yl)-propane, 2-methyl-1-[N-methyl-N-(4-chloro-3-trifluoromethylphenylmercapto)]-carbamoyloximino-1-(1,2,4-triazol-1-yl)-propane, 2-methyl-1-[N-methyl-N-(4-chloro-3-trifluoromethylphenylmercapto)]-carbamoyloximino-1-(pyrazol-1-yl)-propane, N,N'-bis-[2-methyl-1-oximino-carbonyl-1-(1,2,4-triazol-1-yl)-propane]-thio-methylamine, N,N' -bis-[2-methyl-1-oximinocarbonyl-1-(pyrazol-1-yl)-propane]-thio-bis-methylamine, 1-[N-methyl-N-(3-trifluoromethylphenylmercapto)]-carbamoyloximino-1-(1,2,4-triazol-1-yl)-ethane, 1-[N-methyl-N-(3-trifluoromethylphenylmercapto)]-carbamoyloximino-1-(pyrazol-1-yl)-ethane, 1-[N-methyl-N-(4-methylphenylsulphonyl-methylaminomercapto)]-carbamoyloximino-1-(1,2,4-triazol-1-yl)-ethane, 1-[N-methyl-N-(4-methylphenyl-sulphonyl-methylaminomercapto)]-carbamoyloximino-1-(pyrazol-1-yl)-ethane, 1-[N-methyl-N-(4-chlorophenylmercapto)]-carbamoyloximino-1-(1,2,4-triazol-1-yl)-ethane, 1-[N-methyl-N-(4-chlorophenylmercapto)]-carbamoyloximino-1-(pyrazol-1-yl)-ethane, 3,3-dimethyl-2-[N-methyl-N-(4-chloro-3-trifluoromethylphenyl-mercapto)]-carbamoyloximino-1-(1,2,4-triazol-1-yl)-butane, 3,3-dimethyl-2-(N-methyl-N-methylmercapto)-carbamoyloximino-1-(1,2,4-triazol-1-yl)-butane, N,N'-bis-[3,3-dimethyl-2-oximinocarbonyl-1-(1,2,4-triazol-1- yl)-butane]-dithio-bis-methylamine, N,N'-bis-[3-methyl-2-oximinocarbonyl-1-(1,2,4-triazol-1-yl)-butane]-thio-bis-methylamine, 3-methyl-2-(N-methyl-N-dichlorofluoromethylmercapto)-carbamoyloximino-1-(1,2,4-triazol-1-yl)-butane, 3-methyl-2-[N-methyl-N-(3-trifluoromethylphenylmercapto)]-carbamoyloximino-1-(1,2,4-triazol-1-yl)-butane, N,N'-bis-[3,3-dimethyl-2-oximinocarbonyl-1-(1,2,4-triazol-1-yl)-pentane]-thio-bis-methylamine, N,N'-bis-[2-(1-methylcyclohexyl)-2-oximinocarbonyl-1-(1,2,4-triazol-1-yl)-ethane]-thio-bis-methylamine, N,N'-bis-[2-cyclohexyl-2-oximinocarbonyl-1-(1,2,4-triazol-1-yl)-ethane]-thio-bis-methylamine, N,N'-bis-[3-ethyl-2-oximinocarbonyl-1-(1,2,4-triazol-1-yl)-pentane]-thio-bis-methylamine, 3,3-dimethyl-2-[N-methyl-N-(3-trifluoromethylphenylmercapto)]-carbamoyloximino-1-(1,2,4-triazol-1-yl)-pentane and 2-cyclohexyl-2-[N-methyl-N-(4-chlorophenylmercapto)]-carbamoyl-oximino-1-(1,2,4-triazol-1-yl)-ethane.

As already mentioned, the active compounds according to the invention are distinguished by excellent insecticidal, acaricidal and nematocidal activity. In addition, they also possess a certain arthropod metamorphosis-inhibiting action as well as a certain fungicidal action.

The active compounds are well tolerated by plants, have a favorable level of toxicity to warm-blooded animals, and can be used for combating arthropod pests, especially insects and arachnids, and nematodes which are encountered in agriculture, in forestry, in the protection of stored products and of materials, and in the hygiene field. They are active against normally sensitive and resistant species and against all or some stages of development. The above-mentioned pests include: from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec,; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp., and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Erisoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., and Psylla spp.; from the order of the Lepidoptera, for example *Pectinophora gossypiella, Bupalus piniarius,* *Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aenus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp., from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Tabanus spp., Tannia spp., *Bibio hortulanus, Oxcinella frit,* Stomoxys spp., Oestrus spp., Hypoderma spp., Phorbia spp. *Pegomyia hyoscyami, Ceratitis capitata, Dacus oleae* and *Tipula paludoas;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Byrobia praetiosa,* Panonychus spp., and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water, as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant-protection agents, such as other arthropodicides, nematicides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods and nematodes which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present inven-

EXAMPLE 1

(a) Preparation of the starting material:

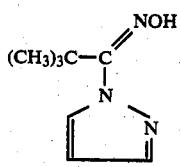

75 g (1.1 mol) of pyrazole and 101 g (1 mol) of triethylamine were dissolved in 500 ml of absolute tetrahydrofuran and cooled to 0° C. 135.5 g (1 mol) of pivalohydroxamic acid chloride in 100 ml of absolute tetrahydrofuran were added dropwise. The mixture was then stirred for a further 12 hours at about 20° C. The salt which had separated out was filtered off, the filtrate was concentrated by distilling off the solvent in vacuo and the residue was also distilled. 88.5 g (53% of theory) of 2,2-dimethyl-1-oximino-1-(pyrazol-1-yl)-propane of boiling point b.p.=82°–85° C./0.12 mm Hg and of melting point 68°–71° C. were obtained.

(b) 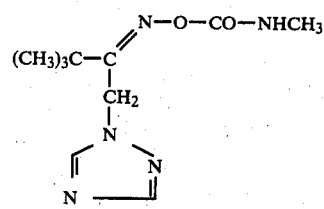 (1)

Process variant (a)

8.35 g (0.05 mol) of 2,2-dimethyl-1-oximino-1-(pyrazol-1-yl)-propane and 11.3 g (0.05 mol) of N-methyl-N-trichloromethylsulphenyl-carbamic acid fluoride were initially introduced into 100 ml of anhydrous dioxane and 5.05 g (0.05 mol) of triethylamine were added dropwise at 20° to 30° C., while stirring. After standing for 3 hours at room temperature, the reaction mixture was poured into ice-water and the precipitate which had separated out was filtered off. After recrystallization from petroleum ether, 12.5 g (67% of theory) of 2,2-dimethyl-1-(N-methyl-N-trichloromethyl-mercapto)-carbamoyloximino-1-(pyrazol-1-yl)-propane of melting point 99°–100° C. were obtained.

EXAMPLE 2

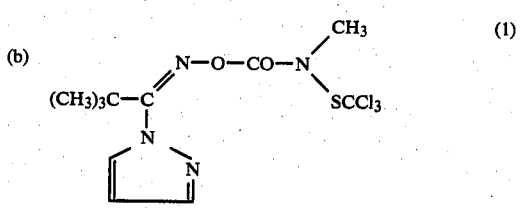 (2)

Process variant (a)

5.05 g (0.05 mol) of triethylamine were added dropwise, while stirring, to 9.1 g (0.05 mol) of 3,3-dimethyl-2-oximino-1-(1,2,4-triazol-1-yl)-butane and 4.6 g (0.025 mol) of N,N'-bis-(fluorocarbonyl)-thio-bis-methylamine in 70 ml of anhydrous dioxane, at 20° to 30° C. After standing for 12 hours at room temperature, the reaction mixture was poured into ice-water and was repeatedly extracted with methylene chloride. The combined methylene chloride phases were dried over sodium sulphate and concentrated by distilling off the solvent in vacuo. The oily residue was taken up in acetone and excess naphthalene-1,5-disulphonic acid was added. The crystalline precipitate which separated out was filtered off and washed with acetone. 6.3 g (32% of theory) of N,N'-bis-[3,3-dimethyl-2-oximinocarbonyl-1-(1,2,4-triazol-1-yl)-butane]-thio-bis-methylamine-naphthalene-1,5-disulphonic acid of melting point 173° C. (with decomposition) were obtained.

EXAMPLE 3

(a) Preparation of the starting material:

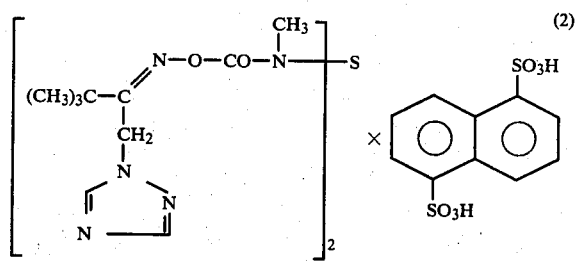

18.2 g (0.1 mol) of 3,3-dimethyl-2-oximino-1-(1,2,4-triazol-1-yl)-butane were dissolved in 100 ml of methylene chloride and 11.4 g (0.2 mol) of methyl isocyanate were added while stirring. The mixture was left to stand overnight at room temperature and the volatile constituents were then distilled off in vacuo. The oily residue was caused to crystallize by trituration with petroleum ether. After recrystallization from ethyl acetate/petroleum ether, 19.2 g (80% of theory) of 3,3-dimethyl-2-methylcarbamoyloximino-1-(1,2,4-triazol-1-yl)-butane of melting point 94°–96° C. were obtained.

(b) 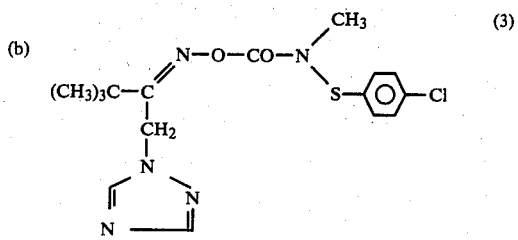 (3)

Process variant (b) 8.9 g (0.036 mol) of 3,3-dimethyl-2-methylcarbamoyloximino-1-(1,2,4-triazol-1-yl)-butane and 3 g of pyridine were dissolved in 100 ml of anhydrous benzene and 10 g (0.055 mol) of p-chlorophenyl-sulphenyl chloride were added at 20° C. to 30° C., while stirring. The mixture was stirred for a further 16 hours at room temperature. The benzene phase was washed with water and sodium bicarbonate solution, dried over sodium sulphate and concentrated. The crystalline residue was recrystallized from benzene/cyclohexane. 6.5 g (46.5% of theory) of 3,3-dimethyl-2-[N-methyl-N-(4-chlorophenylmercapto)]-carbamoyloximino-1-(1,2,4-triazol-1-yl)-butane of melting point 138°–140° C. were obtained.

The compounds in Table 1, which follows, were obtained analogously:

TABLE 1

$$R-\underset{R^1}{C}=N-O-CO-N\underset{(S)_n-R^3}{\overset{R^2}{\diagdown}}, \quad (I)$$

| Compound No. | R | R¹ | R² | n | R³ | Melting point (°C.) or refractive index |
|---|---|---|---|---|---|---|
| 4 | $(CH_3)_3C-$ | -N(pyrazole-CH₃) | $CH_3$ | 1 | $-CCl_3$ | 102–104 |
| 5 | $(CH_3)_3C-$ | -N(pyrazole-Cl) | $CH_3$ | 1 | $-CCl_3$ | 96–97 |
| 6 | $(CH_3)_3C-$ | -N(pyrazole) | $CH_3$ | 1 | dimer | 105–110 |
| 7 | $(CH_3)_3C-$ | -N(pyrazole) | $CH_3$ | 1 | $-CCl_2F$ | 86–88 |
| 8 | $(CH_3)_3C-$ | -N(pyrazole) | $CH_3$ | 1 | -C₆H₄-CF₃ | $n_D^{22.5}=1.517$ |
| 9 | $(CH_3)_3C-$ | -N(pyrazole) | $CH_3$ | 1 | -C₆H₄-Cl | viscous oil |
| 10 | $(CH_3)_3C-$ | -N(pyrazole) | $CH_3$ | 1 | $-N(CH_3)-SO_2-C_6H_4-CH_3$ | viscous oil |
| 11 | $(CH_3)_3C-$ | -N(imidazole) | $CH_3$ | 1 | $-CCl_3$ | 83–86 |
| 12 | $(CH_3)_3C-$ | -N(1,2,4-triazole) | $CH_3$ | 1 | $-CCl_3$ | 115–116 |
| 13 | $(CH_3)_3C-$ | -N(triazole-Cl) | $CH_3$ | 1 | $-CCl_3$ | 90–91 |
| 14 | $(CH_3)_3C-$ | -N(triazole) | $CH_3$ | 1 | dimer | 204–205 |

TABLE 1-continued $$\underset{R^1}{\overset{R}{C}}=N-O-CO-N\overset{R^2}{\underset{(S)_n-R^3,}{}} \quad (I)$$

| Compound No. | R | $R^1$ | $R^2$ | n | $R^3$ | Melting point (°C.) or refractive index |
|---|---|---|---|---|---|---|
| 15 | $(CH_3)_3C-$ | $-N\underset{N}{\overset{N=}{\diagup}}$ | $CH_3$ | 2 | dimer | viscous oil |
| 16 | $(CH_3)_3C-$ | $-N\underset{N}{\overset{N=}{\diagup}}$ | $CH_3$ | 1 | $-CO-OCH_3$ | 98–100 |
| 17 | $(CH_3)_3C-$ | $-N\underset{N}{\overset{N=}{\diagup}}$ | $CH_3$ | 1 | $-\text{C}_6\text{H}_4-CF_3$ | 99–100 |
| 18 | $(CH_3)_3C-$ | $-N\underset{N}{\overset{N=}{\diagup}}$ | $CH_3$ | 1 | $-\underset{\overset{|}{CH_3}}{N}-SO_2-\text{C}_6\text{H}_4-CH_3$ | 123–128 |
| 19 | $(CH_3)_3C-$ | $-N\underset{N}{\overset{N=}{\diagup}}$ | $CH_3$ | 1 | $-CCl_2F$ | 91–12 |
| 20 | $(CH_3)_3C-$ | $-N\underset{}{\overset{N=N}{\diagup}}$ | $CH_3$ | 1 | dimer | 170–172 |
| 21 | $(CH_3)_3C-$ | $-N\underset{}{\overset{N=N}{\diagup}}$ | $CH_3$ | 1 | $-CO-OCH_3$ | 80–82 |
| 22 | $(CH_3)_3C-$ | $-N\underset{}{\overset{N=}{\diagup}}$ | $CH_3$ | 1 | $-CO-OCH_3$ | viscous oil |
| 23 | $(CH_3)_3C-$ | $-CH_2-N\underset{Cl}{\overset{N=}{\diagup}}$ | $CH_3$ | 1 | $-CCl_3$ | 75–76 |
| 24 | $(CH_3)_3C-$ | $-CH_2-N\underset{}{\overset{N=}{\diagup}}$ | $CH_3$ | 1 | $-CCl_3$ | 60–61 |
| 25 | $(CH_3)_3C-$ | $-CH_2-N\underset{}{\overset{=N}{\diagup}}$ | $CH_3$ | 1 | $-CCl_2F$ | 184 (× ½ naphthalene-1,5-disulfonic acid) |

TABLE 1-continued $$R-\underset{R^1}{\overset{}{C}}=N-O-CO-\underset{(S)_n-R^3}{\overset{R^2}{N}}, \quad (I)$$

| Compound No. | R | R¹ | R² | n | R³ | Melting point (°C.) or refractive index |
|---|---|---|---|---|---|---|
| 26 | (CH₃)₃C— | —CH₂—N(triazole) | CH₃ | 1 | —CCl₂F | viscous oil |
| 27 | (CH₃)₃C— | —CH₂—N(triazole) | CH₃ | 1 | —CCl₃ | 74–76 |
| 28 | (CH₃)₃C— | —CH₂—N(triazole) | CH₃ | 1 | dimer | viscous oil |
| 29 | (CH₃)₃C— | —CH₂—N(triazole) | CH₃ | 1 | —CO—OCH₃ | 87–88 |
| 30 | (CH₃)₃C— | —CH₂—N(triazole) | CH₃ | 1 | —C₆H₄—CF₃ | 81–86 |
| 31 | (CH₃)₃C— | —CH₂—N(triazole) | CH₃ | 1 | —N(CH₃)—SO₂—C₆H₄—CH₃ | viscous oil |
| 32 | (CH₃)₂CH— | —N(triazole) | CH₃ | 1 | dimer | 139 |
| 33 | (CH₃)₂CH— | —N(triazole) | CH₃ | 1 | —N(CH₃)—SO₂—C₆H₄—CH₃ | Kristallbrei |
| 34 | (CH₃)₂CH— | —N(triazole) | CH₃ | 1 | —CCl₃ | 95–97 |
| 35 | (CH₃)₂CH— | —N(triazole) | CH₃ | 1 | —C₆H₄—Cl | 122–130 |
| 36 | (CH₃)₂CH— | —N(pyrazole) | CH₃ | 1 | —CCl₃ | 100 |

TABLE 1-continued $$R-\underset{R^1}{C}=N-O-CO-N\underset{(S)_n-R^3}{\overset{R^2}{\diagdown}}, \quad (I)$$

| Compound No. | R | R¹ | R² | n | R³ | Melting point (°C.) or refractive index |
|---|---|---|---|---|---|---|
| 37 | (CH₃)₂CH— | -N⟨N=⟩ (pyrazolyl) | CH₃ | 1 | dimer | 123–127 |
| 38 | (CH₃)₂CH— | -N⟨N=⟩ | CH₃ | 1 | —N(CH₃)—SO₂—C₆H₄—CH₃ | viscous oil |
| 39 | (CH₃)₂CH— | -N⟨N=⟩ | CH₃ | 1 | —C₆H₄—Cl | 88–91 |
| 40 | (CH₃)₃C— | -N⟨N=N⟩ (triazolyl) | CH₃ | 1 | —C₆H₄—Cl | 120–121 |
| 41 | (CH₃)₂CH— | -N⟨N=⟩ | CH₃ | 1 | —C₆H₄—CF₃ | viscous oil |
| 42 | (CH₃)₂CH— | -N⟨N=N⟩ | CH₃ | 1 | —C₆H₄—CF₃ | 110–112 |

In the following examples comparing activities, the novel active compounds are each identified by the number, given in brackets, from the corresponding preparative example and Table 1. The known comparison compounds are identified as follows:

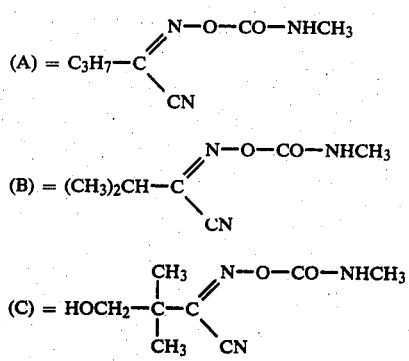

$$(A) = C_3H_7-C\underset{CN}{\overset{N-O-CO-NHCH_3}{\diagup}}$$

$$(B) = (CH_3)_2CH-C\underset{CN}{\overset{N-O-CO-NHCH_3}{\diagup}}$$

$$(C) = HOCH_2-\underset{CH_3}{\overset{CH_3}{\underset{|}{C}}}-C\underset{CN}{\overset{N-O-CO-NHCH_3}{\diagup}}$$

EXAMPLE 4

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plates (*Phaseolus vulgaris*) which were heavily infested with the two spotted spider mide (*Tetranychus urticae*) in all stages of development were sprayed with the preparation of the active compound until dripping wet.

After the specified period of time, the degree of destruction was determined as a percentage: 100% meant that all the spider mites were killed whereas 0% meant that none of the spider mites were killed.

The active compounds, the concentrations of the active compounds, the evaluation times and the results can be seen from the following table:

TABLE 2

| | (mites which damage plants) Tetranychus test. | |
|---|---|---|
| Active Compound | Active Compound concentration in %. | Degree of destruction in % after 2 days. |
| (A) | 0.1 | 0 |
| (B) | 0.1 | 0 |
| (C) | 0.1 | 0 |
| (21) | 0.1 | 100 |
| (16) | 0.1 | 99 |
| (12) | 0.1 | 85 |

TABLE 2-continued

| | (mites which damage plants) Tetranychus test. | |
|---|---|---|
| Active Compound | Active Compound concentration in %. | Degree of destruction in % after 2 days. |
| (7) | 0.1 | 98 |
| (20) | 0.1 | 80 |
| (15) | 0.1 | 100 |

EXAMPLE 5

Phaedon larvae test:

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all the beetle larvae had been killed whereas 0% meant that none of the beetle larvae had been killed.

The active compounds, the concentrations of the active compounds, the evaluation times and the results can be seen from the following table:

TABLE 3

| | (insects which damage plants) Phaedon larvae test | |
|---|---|---|
| Active compounds | Active compound concentration in % | Degree of destruction in % after 3 days. |
| (A) | 0.1 | 100 |
| | 0.01 | 0 |
| (B) | 0.1 | 100 |
| | 0.01 | 0 |
| (C) | 0.1 | 80 |
| | 0.01 | 0 |
| (21) | 0.1 | 100 |
| | 0.01 | 100 |
| (16) | 0.1 | 100 |
| | 0.01 | 100 |
| (1) | 0.1 | 100 |
| | 0.01 | 100 |
| (5) | 0.1 | 100 |
| | 0.01 | 90 |
| (12) | 0.1 | 100 |
| | 0.01 | 90 |
| (13) | 0.1 | 100 |
| | 0.01 | 100 |
| (7) | 0.1 | 100 |
| | 0.01 | 100 |
| (8) | 0.1 | 100 |
| | 0.01 | 100 |
| (17) | 0.1 | 100 |
| | 0.01 | 100 |
| (6) | 0.1 | 100 |
| | 0.01 | 100 |
| (20) | 0.1 | 100 |
| | 0.01 | 100 |
| (14) | 0.1 | 100 |
| | 0.01 | 100 |
| (15) | 0.1 | 100 |
| | 0.01 | 100 |

EXAMPLE 6

Root-systemic action

Test larvae: *Phaedon cochleariae*
Solvent: 3 parts by weight of acetone
Emulsifier: 1 part by weight of alkylaryl polyglycol ether To produce a suitable preparation of active compound 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount by weight of active compound per unit volume of soil, which is given hereinafter in ppm (=mg/liter), was decisive. The treated soil was filled into pots and these were planted with cabbage (*Brassica oleracea*). The active compound could in this way be absorbed from the soil by the roots of the plants and be transported into the leaves.

In order to demonstrate the root-systemic effect, exclusively the leaves were infested with the above-mentioned test larvae after 7 days. After a further 2 days, the evaluation was carried out by counting or estimating the dead larvae. The root-systemic action of the active compound was derived from the mortality figures. It was 100% if all the test larvae had been killed and 0% if just as many test larvae survived as in the case of the untreated control.

The active compounds, the amounts used and the results can be seen from the table which follows:

TABLE 4

| Root-systemic action Phaedon cochleariae larvae | |
|---|---|
| Active compound | Degree of destruction in % at an active compound concentration of 20 ppm. |
| (C) | 0% |
| (12) | 100% |
| (14) | 100% |
| (15) | 100% |
| (17) | 100% |
| (20) | 100% |
| (21) | 100% |
| (6) | 100% |
| (8) | 100% |
| (16) | 100% |
| (26) | 100% |
| (27) | 100% |
| (28) | 100% |
| (2) | 100% |
| (29) | 100% |
| (30) | 100% |
| (3) | 100% |

EXAMPLE 7

Root-systemic action

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of weight of active compound per unit volume of soil, which is given hereinafter in ppm (=mg/liter), was decisive. The treated soil was filled into pots and these were planted with cabbage (*Brassica oleracea*). The active compound could in this was by absorbed from the soil by the roots of the plants and be transported into the leaves.

In order to demonstrate the root-systemic effect, exclusively the leaves were infested with the above-mentioned test insects after 7 days. After a further 2 days, the evaluation was carried out by counting or estimating the dead insects. The root-systemic action of the active compound was derived from the mortality figures. It was 100% if all the test insects had been killed and 0% if just as many test insects survived as in the case of the untreated control.

The active compounds, the amounts used and the results can be seen from the table, which follows:

TABLE 5

| Active compound | Root-systemic action Myzus persicae Degree of destruction in % at an active compound concentration of 20 ppm |
|---|---|
| (C) | 0% |
| (12) | 100% |
| (14) | 100% |
| (15) | 100% |
| (17) | 100% |
| (16) | 100% |
| (20) | 100% |
| (21) | 100% |
| (1) | 100% |
| (6) | 100% |
| (7) | 100% |
| (8) | 100% |
| (28) | 100% |
| (2) | 100% |
| (29) | 100% |
| (30) | 100% |
| (3) | 100% |
| (27) | 100% |

EXAMPLE 8

Test insect: *Phorbia antiqua* grubs in the soil
Solvent: 3 parts by weight of acetone
Emulsifier: 1 part by weight of alkylaryl polyglycolether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The soil was filled into pots and the pots were left to stand at room temperature.

After 24 hours the test insects were introduced into the treated soil and after a further 2 to 7 days the degree of effectiveness of the active compound was determined in % by counting dead and live test insects. The degree of effectiveness was 100% if all the test insects had been killed and was 0% if exactly as many test insects were still alive as in the case of the of the untreated control.

The active compounds, amounts used and results can be seen from the table which follows:

TABLE 6

| Active compound | Soil insecticides. Phorbia antiqua grubs in the soil Degree of destruction in % at an active compound concentration of 20 ppm. |
|---|---|
| (C) | 0% |
| (13) | 100% |
| (14) | 100% |
| (16) | 100% |
| (21) | 100% |
| (5) | 100% |

EXAMPLE 9

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit of soil, which is hereinafter given in ppm (=mg/l), was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

TABLE 7

| Active compound | Nematicides (Meloidogyne incognita) Degree of destruction in % at an active compound concentration of 20 ppm |
|---|---|
| (C) | 0% |
| (12) | 100% |
| (13) | 100% |
| (14) | 100% |
| (15) | 100% |
| (17) | 100% |
| (16) | 100% |
| (20) | 100% |
| (21) | 100% |
| (11) | 100% |
| (26) | 100% |
| (27) | 100% |
| (28) | 100% |
| (2) | 100% |

TABLE 7-continued

| | Nematicides |
|---|---|
| | (*Meloidogyne incognita*) |
| Active compound | Degree of destruction in % at an active compound concentration of 20 ppm |
| (29) | 100% |
| (30) | 100% |
| (3) | 100% |

It will be appreciated that the instant specification and examples are set forth by way of illustration and not limitation, and that various modifications and changes may be made without departing from the spirit and scope of the present invention.

What is claimed is:

1. An N-sulphenylated oxime-carbamate of the formula

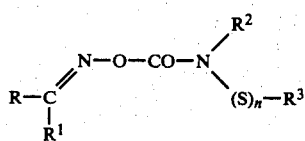

in which
R is alkyl with 1 to 6 carbon atoms, phenyl, phenyl substituted by halogen, phenyl-$C_{1-4}$-alkyl-, halophenyl-$C_{1-4}$-alkyl-, or cycloalkyl, methylcycloalkyl or ethyl-cycloalkyl with 5 to 7 ring carbon atoms;
$R^1$ is (a) a pyrazol-1-yl, imidazol-1-yl, 1,2,4-triazol-1-yl, 1,2,3-triazol-1-yl, 1,3,4-triazol-1-yl, 1,2,5-triazol-1-yl, indazol-1-yl, benzimidazol-1-yl, or benztriazol-1-yl radical optionally carrying at least one halogen, alkyl with 1 to 4 carbon atoms, halogenoalkyl with up to 2 carbon atoms and up to 5 halogen atoms, alkoxy or alkylthio each with up to 4 carbon atoms, or nitro substituent; or (b) alkyl with 1–4 carbon atoms or cycloalkyl with 5–6 carbon atoms, either of which is substituted by (a);
$R^2$ is alkyl with 1 to 4 carbon atoms;
$R^3$ is alkyl with 1 to 4 carbon atoms, halogenoalkyl with 1 or 2 carbon atoms and up to 5 halogen atoms, phenyl, phenyl substituted by halogen, alkyl with 1 or 2 carbon atoms or halogenoalkyl with 1 or 2 carbon atoms and up to 5 halogen atoms, alkoxycarbonyl with 1 to 4 carbon atoms in the alkoxy part, a radical identical to that to which the $-(S)_n R^3$ group is bonded, or $-NR^5-SO_2-R^4$,
$R^4$ is alkyl with 1 to 4 carbon atoms, dialkylamino with 1 to 4 carbon atoms in each alkyl part, phenyl, or phenyl substituted by halogen, alkyl with 1 or 2 carbon atoms, halogen-alkyl with 1 or 2 carbon atoms and up to 5 halogen atoms, cyano or nitro,
$R^5$ is alkyl with 1 to 4 carbon atoms, and
n is 1 or 2,
or a salt thereof with a physiologically tolerated acid.

2. The compound according to claim 1 wherein such compound is
2,2-dimethyl-1-(N-methyl-N-dichlorofluoromethylmercapto)-carbamoyloximino-1-(pyrazol-1-yl)-propane of the formula

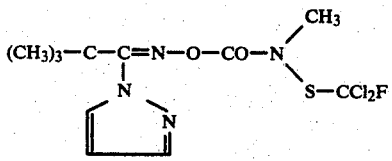

or a salt thereof.

3. The compound according to claim 1 wherein such compound is
N,N'-bis-[2,2-dimethyl-1-oximino-carbonyl-1-(1,2,4-triazol-1-yl)-propane]-thio-bis-methylamine of the formula

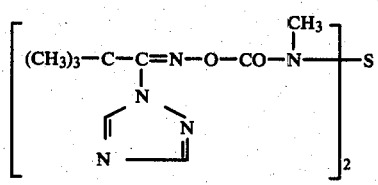

or a salt thereof.

4. The compound according to claim 1 wherein such compound is
2,2-dimethyl-1-[N-methyl-N-(4-methylphenylsulphonylmethylaminomercapto)]-carbamoyloximino-1-(1,2,4-triazol-1-yl)-propane of the formula

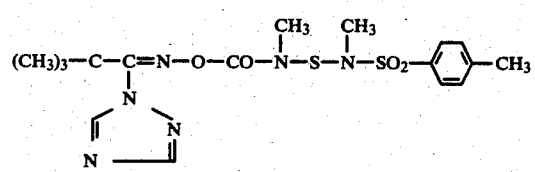

or a salt thereof.

5. The compound according to claim 1 wherein such compound is
N,N'-bis-[3,3-dimethyl-2-oximino-carbonyl-1-(1,2,4-triazol-1-yl)-butane]-thio-bis-methylamine of the formula

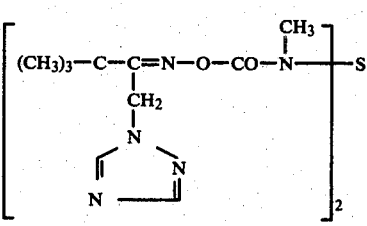

or a salt thereof.

6. The compound according to claim 1 wherein such compound is
N,N'-bis-[2-methyl-1-oximino-carbonyl-1-(1,2,4-triazol-1-yl)-propane]-thio-bis-methylamine of the formula

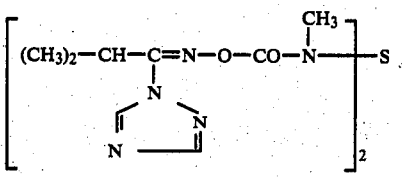

or a salt thereof.

7. An arthropodicidal or nematicidal composition containing as active ingredient an arthropodicidally or nematicidally effective amount of a compound or salt thereof according to claim 1 in admixture with a diluent.

8. A method of combating arthropods or nematodes, which comprises applying to the arthropods or nematodes, or to a habitat thereof, an arthropodicidally or nematicidally effective amount of a compound or salt thereof according to claim 1.

9. The method according to claim 8 in which said compound is
2,2-dimethyl-1-(N-methyl-N-dichlorofluoromethylmercapto)-carbamoyloximino-1-(pyrazol-1-yl)-propane,
N,N'-bis-[2,2-dimethyl-1-oximino-carbonyl-1-(1,2,4-triazol-1-yl)-propane]-thio-bis-methylamine,
2,2-dimethyl-1-[N-methyl-N-(4-methylphenylsulphonylmethylaminomercapto)]-carbamoyloximino-1-(1,2,4-triazol-1-yl)-propane,
N,N'bis-[3,3-dimethyl-2-oximino-carbonyl-1-(1,2,4-triazol-1-yl)-butane]-thio-bis-methylamine, or
N,N'-bis-[2-methyl-1-oximino-carbonyl-1-(1,2,4-triazol-1-yl)-propane]-thio-bis-methylamine,
or a salt thereof.

* * * * *